(12) United States Patent
Haider

(10) Patent No.: US 6,565,567 B1
(45) Date of Patent: *May 20, 2003

(54) PEDICLE SCREW FOR OSTEOSYNTHESIS

(76) Inventor: Thomas T. Haider, 2357 Knob Hill Dr., Riverside, CA (US) 92506

( * ) Notice: Subject to any disclaimer, the term of this patent is extended or adjusted under 35 U.S.C. 154(b) by 195 days.

This patent is subject to a terminal disclaimer.

(21) Appl. No.: 09/642,629

(22) Filed: Aug. 18, 2000

Related U.S. Application Data

(63) Continuation-in-part of application No. PCT/US97/23851, filed on Dec. 19, 1997, which is a continuation-in-part of application No. 08/771,133, filed on Dec. 20, 1996, now Pat. No. 5,782,833.

(51) Int. Cl.⁷ .............................................. A61B 17/70
(52) U.S. Cl. ........................... 606/61; 403/90; 403/274
(58) Field of Search ...................... 606/61, 73; 403/90, 403/274, 284

(56) References Cited

U.S. PATENT DOCUMENTS

| | | | | |
|---|---|---|---|---|
| 4,708,510 A | * | 11/1987 | McConnell et al. | 403/90 |
| 5,005,562 A | * | 4/1991 | Cotrel | 128/69 |
| 5,098,432 A | * | 3/1992 | Wagenknecht | 606/54 |
| 5,154,719 A | * | 10/1992 | Cotrel | 606/73 |
| 5,284,398 A | * | 2/1994 | Sakai | 403/135 |
| 5,385,583 A | * | 1/1995 | Cotrel | 623/17 |
| 5,474,555 A | * | 12/1995 | Puno et al. | 606/73 |
| 5,672,176 A | * | 9/1997 | Biedermann et al. | 606/61 |
| 5,743,669 A | * | 4/1998 | Fujita et al. | 403/131 |
| 5,776,134 A | * | 7/1998 | Howland | 606/61 |
| 5,782,833 A | * | 7/1998 | Haider | 606/61 |
| 5,879,350 A | * | 3/1999 | Sherman et al. | 606/61 |
| 5,888,221 A | * | 3/1999 | Gelbard | 623/17 |

\* cited by examiner

*Primary Examiner*—Eduardo C. Robert
*Assistant Examiner*—David Comstock
(74) *Attorney, Agent, or Firm*—Harold L. Jackson

(57) ABSTRACT

A pedicle screw assembly for use with a rod for the immobilization of bone segments. The assembly is composed of a screw, a polyaxial housing for receiving the screw, a washer, a set screw, and a cup-shaped cap. The lower portion of the housing terminates in a reduced cross-sectional area, which engages the bottom of the screw head. When the screw is placed inside the polyaxial housing and the screw is secured into the bone, the polyaxial housing is pivotable with three degrees of freedom. The housing includes a top portion with a pair of upstanding internally threaded posts. A washer is inserted between the head of the screw and the rod. A cap, having a bottom, with a pair of posts accommodating openings and a lateral cross connector, is placed over the posts so that the cross connector engages the rod. The cross connector and washer have concave generally semicylindrical rod engaging surfaces to prevent the rod from rotating or sliding within the housing once the set screw is tightened. A set screw is threaded into the housing posts to secure the rod within the housing. The washer has a roughened lower surface which in conjunction with the reduced cross-sectional area at the bottom of the housing securely clamp and lock the housing to the screw head when the set screw is tightened.

15 Claims, 3 Drawing Sheets

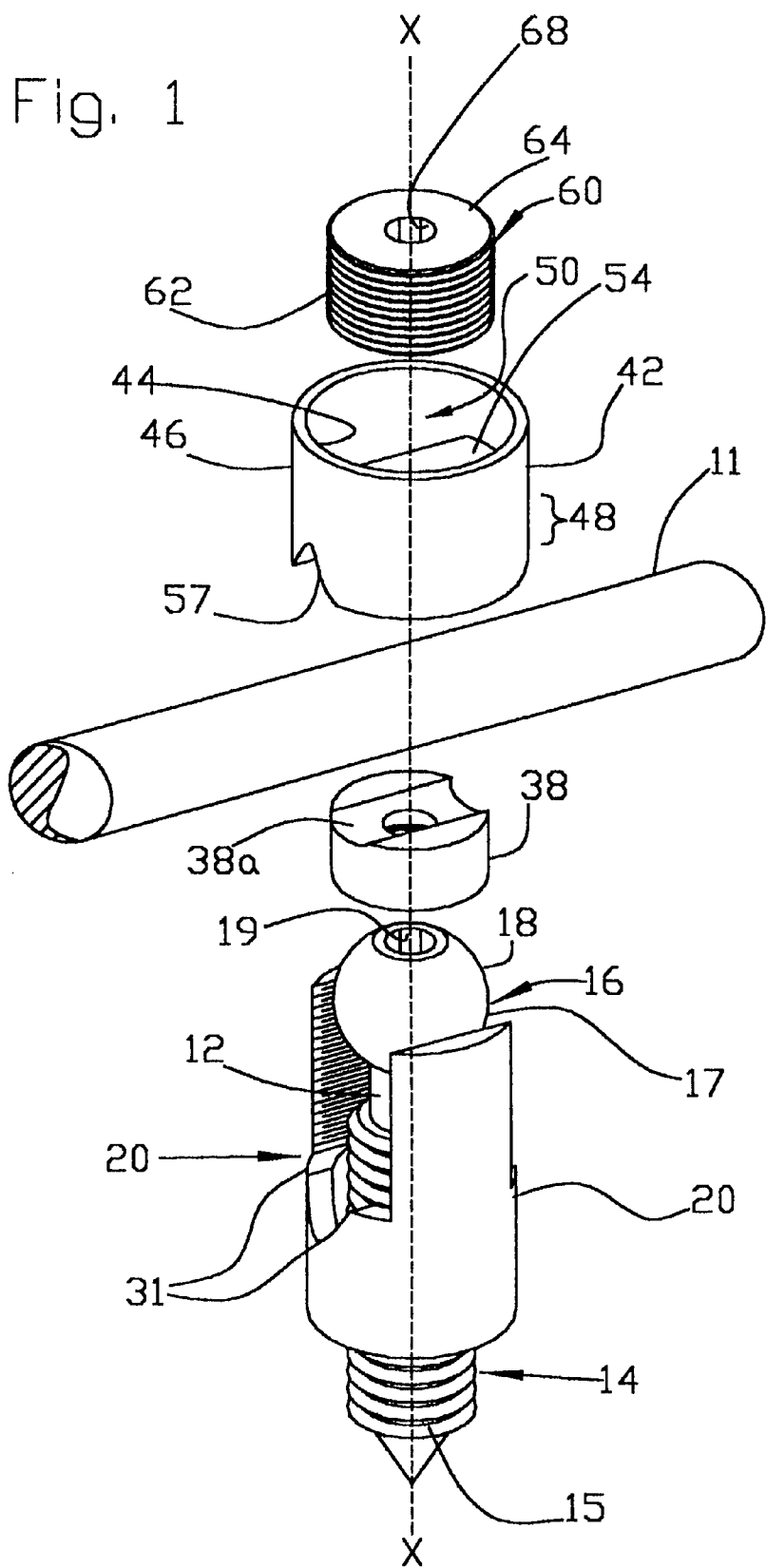

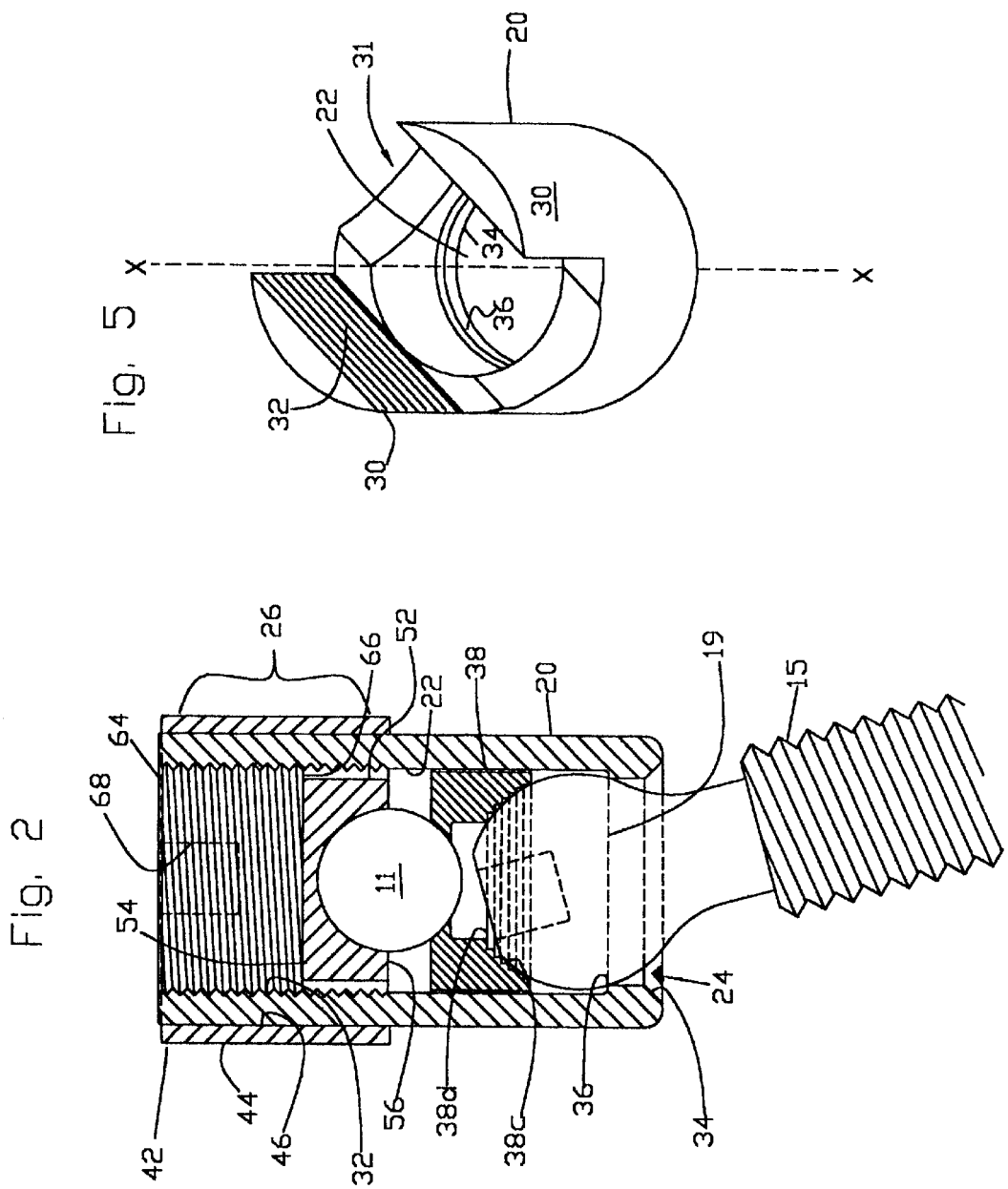

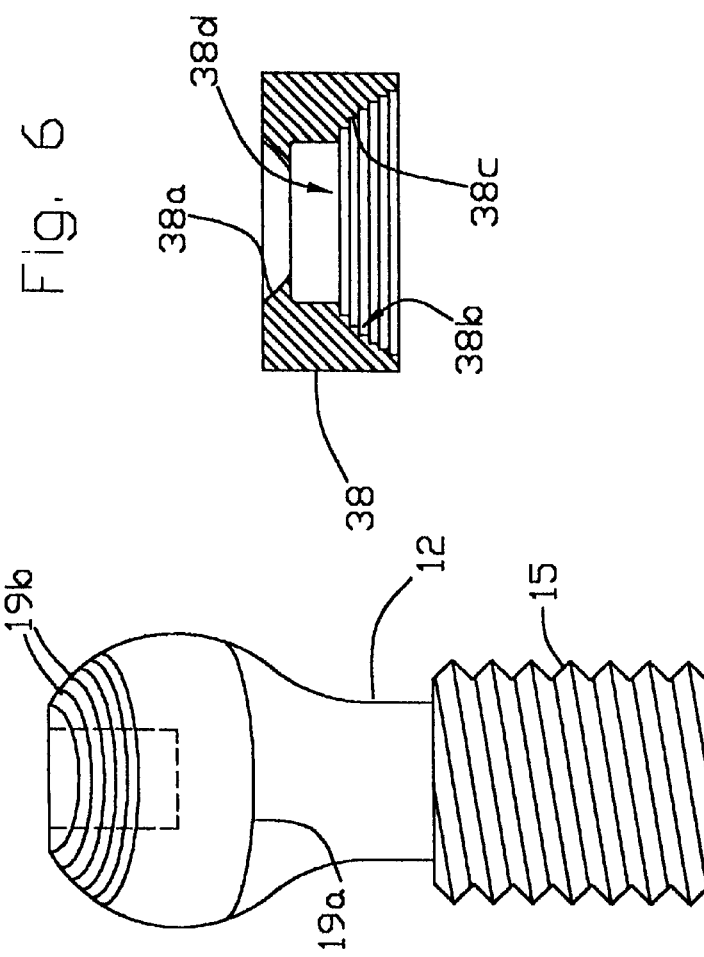
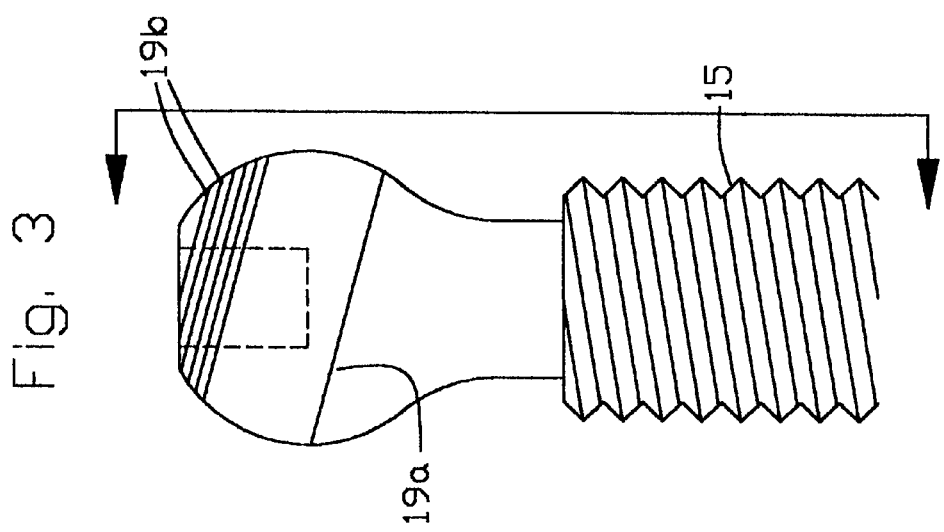

US 6,565,567 B1

PEDICLE SCREW FOR OSTEOSYNTHESIS

RELATED APPLICATION

This application is a continuation-in-part of my pending International PCT application No. PCT/US97/23851 filed Dec. 19, 1997 now U.S. application Ser. No. 09/582,836 filed Jun. 20, 2000 which in turn is a continuation-in-part of my application Ser. No. 08/771,133 filed Dec. 20, 1996 entitled Pedicle Screw System for Osteosynthesis which issued as U.S. Pat. No. 5,782,833.

FIELD OF THE INVENTION

The present invention relates to the medical field commonly referred to as Osteosynthesis, i.e., the fusion between segments of the spine and more particularly to a pedicle screw and rod system for immobilizing the segments during the fusion process.

BACKGROUND OF THE INVENTION

Osteosynthesis is achieved by immobilizing the bone. When trying to achieve osteosynthesis and specifically fusion between different segments of the spine, one has to provide some type of immobilization. There are various prior art systems which try to achieve this purpose. The different systems involve placement of screws into the bone. The screws are then connected to each other by use of various sizes of rods or a plate. The bone segments that are being connected, especially in the spine, may be carrying different angles and different medical-lateral positions. Placement of a rod with a rigid screw or placement of a plate between two rigid screws is difficult because of the medial lateral displacement or angulation at different segments. One has to bend the rod or plate and at times achieve a complex bend in order to connect two different segments of the bone and especially two different areas in the spine. When dealing with the spine, the screws are ordinarily placed into the pedicle, and due to the different positions of the pedicle and different angulations of the screw as it enters the pedicle, one encounters difficulty in positioning and connecting these screws at various points.

Even though one can create a complex bend at the rod or the plate in order to connect two or more screws, there are places in the pedicle where one runs the chance of stress risers at different points and breakage of the system as the bends can never be perfect.

A screw system, which is capable of accommodating the rod in a perfect location without creating any appreciable areas of stress riser, will alleviate some of the above problems. Such a screw system would allow the rod to be bent to achieve fixation between two different points while adjusting to any imperfections in the bend.

There is at least one polyaxial screw system that has been used in the past which will achieve some of these goals; however, there are some inherent problems with this particular system. This polyaxial screw has many components which makes placement of such a screw cumbersome, which in turn, lengthens the operative time for this particular procedure. The system has a locking screw on the inside as well as a locking nut on the outside of the housing, which causes the operation to take much longer to perform. The fixation point which will lock the polyaxial screw and keep it from angling once the system is tightened is also not ideal.

Several patents teach the use of a pedicle screw system which appear to provide several degrees of freedom (i.e., rotation and limited angular deflection about a fixed point) for the immobilization of bone segments. See for example U.S. Pat. No. 5,360,431 ("'431 patent") to Puno et al, U.S. Pat. No. 5,443,467 ("'467 patent") to Biedermann et al, U.S. Pat. No. 5,176,678 ("'678 patent") to Tsou and U.S. Pat. No. 5,206,678 ("Harms patent") to Harms et al. Each of these patented structures has certain drawbacks including the use of a conventional nut to secure the rod into place for support of the bone segments. The nuts have flat surrounding edges which are engaged by a wrench to tighten the nut. Due to the surrounding tissue, and the confined area, difficulty can arise in placing the nut in the correct position thus requiring even more time to perform the operation. During the operation the patient is under anesthesia and this extra time increases the risk to the patient. Also, when secured the nut protrudes into the surrounding soft tissue after the operation is completed. This protrusion can lead to irritation of the surrounding soft tissue and possibly inflammation.

Another problem arising with the use of the nut is the tightening process. The nut is secured through the use of a wrench. The wrench requires space around the nut to be operable which necessarily increases the scope of the surgical procedure. Furthermore, the wrench should not come into contact with the surrounding soft tissue to avoid the possibility of peripheral tissue damage. These limitations tend to further increase the risk to the patient during the operation.

The Harms patent relies on nuts threaded on the immobolizing rod to clamp the rod housing and the head of a pedicle screw together. In addition, the structure of this patent relies on a frictional engagement between the screw head, housing and a compression member to prevent relative movement between the housing and screw head when the nuts are tightened. I have discovered that the reliance on frictional forces in this type of arrangement is not satisfactory.

There is a need for a more reliable pedicle screw and rod system which may readily and rapidly be secured in place, with less bulky equipment and which is less intrusive to the surrounding soft tissue.

SUMMARY OF THE INVENTION

The present invention addresses the stabilization of bone segments through the use of a polyaxial pedicle screw assembly and rod. The rod is arranged to be secured between two or more embedded screw assemblies to immobilize segments of the spine. The assembly includes a screw which has a head and a threaded cylindrical shaft which is adapted to be threaded into the bone. The head of the screw has a top and bottom, both of which are generally spherically convex in shape with the bottom surface of the head merging into the shaft. The head of the screw is larger than the diameter of the cylindrical shaft. The top of the screw head has a wrench engaging surface, such as an allen wrench socket.

The screw fits within a polyaxial housing having a bore aligned along a longitudinal axis for receiving the screw and a lateral opening or bore aligned perpendicular to the longitudinal axis for receiving the rod. The polyaxial housing is divided into two sections. The top section of the housing receives the entire screw including the head and is formed by a pair of spaced upstanding opposed posts which define the lateral opening, generally U-shaped, for receiving the rod. The inner walls of the posts are threaded for receiving a set screw which secures the rod in place. The lower section of the housing terminates in a reduced cross-sectional area, preferably formed by an inwardly projecting annular shoulder, for engaging the bottom of the screw head along a line circumscribing the generally semispherical bottom surface thereof to retain the screw head within the housing. The screw, after insertion into the polyaxial housing, is threadably secured into the bone.

A washer, with a generally spherically concave bottom surface to engage the head of the screw, is then placed within the housing. Preferably the bottom surface of the washer is provided with a roughened surface, such as asperities in the form of sharp edges to provide a locking action between the washer and the screw head in the assembled condition. The top of the washer is provided with a concave surface, preferably semicylindrical or saddle shaped, to conform to the shape of the rod.

The lower surface of the washer and the terminal end of the housing provide for positive gripping surface action with the screw head thereby adding to the stability of the rod and screw, once in place.

The screw assembly further includes a cup-shaped cap having two opposing openings to receive the posts and a cross-connector extending across the bottom of the cap. The cross-connector has a generally flat top surface and a bottom with a concave semi-cylindrical or longitudinal saddle shape to conform to the shape of the rod. The bottom surface of the cross connector preferably provides and interference fit with the upper surface of the rod to prevent relative movement between the rod and the housing in the assembled condition. The radius of curvature of the bottom semi-cylindrical surface of the cross connector may be slightly smaller than the radius of the rod to form the interference fit. The cup-shaped cap is adapted to be placed over the polyaxial housing with the bottom surface of the cross-connector making contact with the rod.

A set screw of conventional configuration is arranged to be threaded into the top section of the polyaxial housing by means of a wrench inserted into a wrench engaging surface, such as an allen wrench socket, in the top of the set screw, to tighten the assembly into place.

With the set screw in place, but not tightened, the assembly has three degrees of freedom, i.e., rotatable and angularly positionable about the head of the screw. The tightening of the set screw secures the assembly into a single position. The set screw allows the assembly to be tightened while overcoming the disadvantage of potential soft tissue damage due to the use of a nut. The screw assembly of the present invention when secured in place does not protrude into the surrounding soft tissue and thus reduces the risk of irritation and soft tissue damage.

The present invention provides a highly flexible and stable bone segment immobilization system with a minimum number of components which results in a reduction in the time that a patient must remain under anesthesia.

The construction and operational features of the present invention may best be understood by reference to the following description taken in conjunction with the appended drawings in which like components in the several figures are identified by the same reference numerals.

BRIEF DESCRIPTION OF THE DRAWINGS

FIG. 1 is an exploded view of a pedicle screw assembly and rod in accordance with the present invention;

FIG. 2 is a cross-sectional view of the assembled pedicle screw system showing only a portion of the screw shaft;

FIGS. 3 and 4 are elevational views (from each side) of the screw head and partial shaft showing the lines of engagement between the head of the screw and the locking ridges formed on the lower surface of the washer and the corner of the shoulder at the bottom of the housing;

FIG. 5 is a perspective view of the housing for the screw assembly; and

FIG. 6 is a cross-sectional view of the washer which engages the upper surface of the head of the screw.

DESCRIPTION OF THE PREFERRED EMBODIMENT

Referring now to the drawings and particularly to FIG. 1, a pedicle screw assembly in accordance with the present invention includes a pedicle screw 12 which has a cylindrical shaft 14 threaded at 15, and a head 16 formed integrally with the shaft. The head of the screw has a generally spherical shape, except for the junction of the shaft with the head. The spherical surface of the head of the screw is divided into upper and lower surfaces with each surface (i.e., lower 17 and upper 18) being generally semispherical. The top of the head of the screw includes an indentation in the form of a wrench engaging surface 19. The wrench engaging surface 19 is illustrated in the form of a hexagonal socket for receiving a suitable wrench such as an alien wrench. The wrench engaging surface could also be in the form of a slot for receiving a screwdriver or any other suitable recessed shape. The head of the screw has a diameter which is larger than the diameter of the threaded shaft 14 as is illustrated in FIG. 1.

Referring now to FIGS. 2 and 5, a polyaxial housing 20 includes a bore 22 aligned along a longitudinal axis x-x for accommodating the passage of a screw therethrough except for the head which is retained by a reduced cross-sectional area at the bottom 24 of the housing as will be explained. The top section 26 of the housing includes a pair of upstanding posts 30 which define a lateral opening or slot 31 (substantially perpendicular to the longitudinal axis) for receiving the rod 11. The inside walls 32 of the posts are threaded to receive a set screw, to be described. The housing 20 terminates at its lower end in an inwardly projecting annular shoulder 34 which forms the reduced cross-sectional area for retaining the screw head. The upper edge 36 of the shoulder 34 preferably forms a sharp corner which engages the lower semispherical surface 17 of the screw head 16 along a line circumscribing the bottom surface 17 as is illustrated by the dashed line representing the shoulder corner and by the line 19a on FIGS. 3 and 4. During assembly the screw 14 is placed within the polyaxial housing 20 such that the bottom 17 of the head of the screw comes into contact with the shoulder corner 36 at the bottom end of the housing as is illustrated in FIG 2. The head of the screw is thus captured or retained within the lower portion of the housing 20.

A washer 38 is adapted to be placed between the rod and the upper surface of the head of the screw as is illustrated in FIGS. 1 and 2. The top surface of the washer 38 includes a generally concave semicylindrical rod engaging surface 38a which receives the rod 11. See FIG. 2. The bottom of the washer has a generally concave spherically shaped screw head engaging surface 38b which includes a roughened surface formed by a series of circular sharp edges or ridges 38c. The sharp edges 38c are concentrically arranged in a stair step pattern around the central axis x-x of the housing, in the assembled condition, as is shown in FIG. 2. The stair step pattern of the ridges extends upwardly from the bottom of the washer to a central opening 38d as is best illustrated in FIG. 2. The concentric ridge pattern on the bottom of the washer is shown in FIG. 6. The ridges tend to score the top surface of the screw head along the lines 19b when a set screw, to be described, is tightened to clamp the housing to the screw head. See FIGS. 3 and 4. While seven ridges are illustrated in FIGS. 2 and 6 it should be noted that the number of ridges can vary.

A cup-shaped cap 42, having cylindrical outer and inner surfaces 44 and 46, respectively, is adapted to be placed over the polyaxial housing 20 and engage the top of the rod 11, as is illustrated in FIG. 2. The cap 42 has a bottom section 48 with a pair of spaced arcuate openings 50 for receiving the posts 30 and a cross-connector or lateral beam 52 spanning the lateral width of the lower inside surface of the cap between the openings. See FIGS. 1, 2 and 4. The cross-connector 52 has a top 54 that is generally flat and a bottom 56 that includes a longitudinal concave rod-engaging surface 57 (i.e., semicylindrical, saddle or U-shaped surface). The cap is adapted to be placed over the outside of the polyaxial housing so that the posts 30 extend through the openings 50 thus allowing the cross-connector to be received between the posts and within the lateral opening or slot 31 of the housing. The cup-shaped cap 42 is arranged to proceed downwardly within the longitudinal bore of the polyaxial housing until the rod engaging surface of the cross-connector comes into contact and preferably creates an interference fit with the upper surface of the rod. This interference fit may be provided by forming the lower semicylindrical surface of the cross connector with a smaller radius than the radius of the rod is illustrated in FIG. 9 of co-pending application No. PCT/US97/23851, now U.S. application Ser. No. 09/582,836 Such an interference fit prevents the rod from rotating or sliding when the assembly is clamped together by a set screw to be described. The disclosure of application No. PCT/US97/23851 is incorporated herein by reference.

A conventional set screw 60 completes the pedicle screw assembly. The set screw includes external threads 62, a top 64, and a bottom 66. The top 64 has a hexagonal indentation or recess which serves as a wrench engaging surface 68, i.e., a hexagonal socket. The bottom 66 is flat. When inserted into the longitudinal bore of the polyaxial housing the threads of the set screw come into contact with the threads on the inner walls of the posts 30. As the set screw 60 is tightened, the bottom 66 of the set screw comes into contact with the top 54 of the cross-connector forcing the housing upwardly or the rod downwardly or both until the rod is firmly captured between the head of the implanted screw (including the washer) and the cap.

The sharp edges 38c (forming the roughened bottom concave surface of the washer 38) are forced against the upper surface of the screw head while the sharp corner 36 of the housing shoulder 34 is forced against the lower surface of the screw head when the set screw is tightened to fix and maintain the angular position of the housing relative to the screw. The biting action of the sharp edges 38c and the sharp corner 36 firmly lock the housing in place. Tests have illustrated that such sharp edges tend to score or form discernible lines on the outer surface of the screw head. This action positively locks the housing in place. To enhance this locking action the washer is preferably made with a harder surface than the screw head. For example, the washer is preferably made of heat treated titanium while the screw (and housing) may be made of titanium in a standard annealed condition. Heat treatment of titanium increases its tensile strength and hardness. Such heat treatment may increase the hardness value by about 10 to 20 percent.

Since the set screw fits inside of the polyaxial housing, there is no contact between the set screw and the tissue of the patient. This reduces the risk of tissue damage and allows for a more limited area of surgical intrusion for the installation of the pedicle screw assembly. Further, the wrench engaging surface is more accessible and requires a less bulky wrench or securing device to accomplish the tightening process. These factors lessen the time required for the operation, minimize tissue damage, and utilizes a smaller securing device to fix the assembly into position.

Before the final tightening operation, the polyaxial housing is freely rotatable and angularly displaceable about the head of the implanted screw. This freedom of movement, to accommodate any bends in the rod, is referred to herein as three degrees of freedom. As the proper alignment is achieved, the assembly can be secured in a single desired position by the final tightening of the set screw.

As a result of this procedure, the bone segments are brought into a stable immobilized position.

While titanium is the preferred material for the assembly components, it should be noted that other high strength materials may be used such as stainless steel, providing of course that the material is compatible with the surrounding bone and tissue.

The parameters of the present device may be altered in numerous ways without departing from the spirit and scope of the invention as defined in the appended claims. Therefore, it is intended that the drawing be interpreted as illustrative and not in any way viewed as being a limitation on the invention.

What is claimed is:

1. A pedicle screw assembly for use with a rod for immobilizing bone segments comprising:

a pedicle screw having a threaded shaft for insertion into a bone segment and an enlarged generally spherical head;

a polyaxial housing having a bore with a longitudinal axis therethrough, for accommodating the passage of the threaded shaft there through, the upper portion of the housing including a pair of internally threaded opposed posts defining an opening substantially perpendicular to the bore axis for receiving the rod, the housing terminating at its lower end in a reduced cross sectional area for engaging the bottom of the screw head along a line circumscribing the generally semispherical bottom surface thereof to retain the screw head within the housing;

a washer positioned within the housing between the rod and the top of the screw head, the washer having a generally semispherical roughened bottom surface defined by a plurality of sharp projections; and a set screw for threadably engaging the internally threaded posts to clamp the assembly together, whereby the head of the screw is clamped between the roughened lower surface of the washer and the lower end of the housing.

2. The pedicle screw assembly of claim 1 wherein the lower end of the housing forms an inwardly projecting shoulder having a corner facing the screw head in the assembled condition which corner tends to bite into the lower surface of the screw head when the set screw is tightened.

3. The pedicle screw assembly of claim 2 wherein the washer has a harder surface than the pedicle screw.

4. The pedicle screw assembly of claim 3 wherein the hardness of the washer is about 10% or greater than that of the pedicle screw.

5. The pedicle screw assembly of claim 4 wherein the screw is made of annealed titanium and the washer is made of heat treated titanium.

6. The pedicle screw assembly of claim 5 wherein the washer has a hardness value of about 10 percent greater than the hardness value of the screw.

7. A pedicle screw assembly for use in conjunction with a rod for immobilizing bone segments comprising:

a pedicle screw having a threaded shaft for insertion into a bone segment and an enlarged generally spherically shaped head;

a polyaxial housing having a bore with a longitudinal axis for accommodating the passage of the threaded shaft therethrough, the lower portion of the housing terminating in a reduced cross-sectional area for engaging the bottom of the screw head along a line circumscribing the generally semispherical bottom surface thereof to retain the screw head within the housing, the upper portion of the housing defining a pair of upstanding posts forming a U-shaped slot therebetween to accommodate the rod and having interior threads;

a lateral beam positioned within the U-shaped slot and defining a concave generally saddle-shaped lower surface for engaging the upper surface of the rod;

a washer positioned within the housing between the rod and the head of the screw, the washer having a concave generally saddle-shaped upper surface for engaging the lower surface of the rod and a generally semispherical concave roughened lower surface defined by a plurality of sharp projections thereon for engaging the upper surface of the head of the screw; and means for clamping the assembly together, whereby the head of the screw is clamped between the lower surface of the washer and the reduced cross-sectional area of the housing and the rod is clamped between the lower surface of the lateral beam and the upper surface of the washer.

8. The pedicle screw assembly of claim 7 wherein the clamping means is a set screw.

9. The pedicle screw assembly of claim 7 wherein the lower surface of the lateral beam is semicylindrical in shape with a smaller radius than the radius of the rod to provide an interference fit with the upper surface of the rod to prevent the rod from rotating or sliding within the housing when the set screw is tightened.

10. The pedicle screw assembly of claim 9 wherein the lateral beam forms the lower portion of a cap having opposed openings which fit over the posts on the housing.

11. A pedicle screw assembly for use in conjunction with a cylindrical rod for immobilizing bone segments comprising:

a screw having a threaded shaft for insertion into a bone segment and an enlarged head with a generally convex semispherical top and bottom surface;

a set screw;

a polyaxial housing having a generally cylindrical inside surface of larger diameter than the diameter of the head of the screw and an inwardly projecting shoulder on the lower portion thereof which engages the bottom surface of the head of the screw, the housing including a pair of upstanding posts which form the upper portion of the housing, the posts defining a U-shaped slot therebetween to accommodate the rod and having interior threads for receiving the set screw;

a cup-shaped cap defining diametrically opposed openings which fit over the posts of the housing, the cap having a cross connector extending across the bottom thereof, the cross connector being positioned within the U-shaped slot, between the set screw and the rod, and defining a concave semicylindrical lower surface for gripping the upper surface of the rod; and a washer positioned within the housing between the rod and the head of the screw, the washer having a concave generally semicylindrical upper surface for gripping the lower surface of the rod, and a generally semispherical lower surface for engaging the upper surface of the head of the screw, the lower surface of the cross connector and the upper surface of the washer serving to firmly grasp the rod therebetween when the set screw is tightened to prevent the rod from rotating or moving longitudinally within the housing, the lower surface of the washer having a roughened surface, which roughened surface in conjunction with the inwardly projecting shoulder of the housing serve to grasp the head of the screw and secure the housing in a fixed position relative to the head of the screw when the set screw is tightened.

12. The pedicle screw assembly of claim 11 wherein the lower surface of the washer is formed with a plurality of sharp protruding edges.

13. The pedicle screw assembly of claim 12 wherein the sharp protruding edges form a circular pattern on the semispherical surface of the washer.

14. The pedicle screw assembly of claim 13 wherein the protruding edges define a stair step pattern of concentric circles decreasing in diameter from the bottom to the top of the recess.

15. The pedicle screw assembly of claim 14 wherein the washer has a hardness value greater than the hardness value of the screw.

* * * * *

UNITED STATES PATENT AND TRADEMARK OFFICE
CERTIFICATE OF CORRECTION

PATENT NO. : 6,565,567 B1
DATED : May 20, 2003
INVENTOR(S) : Haider

It is certified that error appears in the above-identified patent and that said Letters Patent is hereby corrected as shown below:

Title page,
Item [57], ABSTRACT,
Line 6, after the words "sectional area," should be the following words -- for example, by an inwardly projecting shoulder, --

Column 4,
Line 21, "alien" should read -- allen --.

Signed and Sealed this

Fourteenth Day of October, 2003

JAMES E. ROGAN
*Director of the United States Patent and Trademark Office*